United States Patent
Ehrenpreis

(12) 
(10) Patent No.: US 8,716,203 B2
(45) Date of Patent: May 6, 2014

(54) WATER-SOLUBLE COLONOSCOPY LUBRICANT

(76) Inventor: Eli D Ehrenpreis, Skokie, IL (US)

( * ) Notice: Subject to any disclaimer, the term of this patent is extended or adjusted under 35 U.S.C. 154(b) by 363 days.

(21) Appl. No.: 12/581,144

(22) Filed: Oct. 18, 2009

(65) Prior Publication Data

US 2011/0092593 A1    Apr. 21, 2011

(51) Int. Cl.
*C10M 141/02* (2006.01)
*A61B 1/04* (2006.01)
*A61K 36/00* (2006.01)

(52) U.S. Cl.
USPC ............... 508/160; 600/117; 424/195.18

(58) Field of Classification Search
None
See application file for complete search history.

(56) References Cited

U.S. PATENT DOCUMENTS

| | | | |
|---|---|---|---|
| 2002/0114776 A1* | 8/2002 | Zaneveld et al. | 424/78.35 |
| 2002/0192273 A1 | 12/2002 | Buseman | |
| 2003/0232090 A1* | 12/2003 | Ahmad et al. | 424/488 |
| 2005/0002927 A1* | 1/2005 | Quay et al. | 424/143.1 |
| 2005/0239742 A1* | 10/2005 | Place et al. | 514/54 |
| 2005/0271598 A1* | 12/2005 | Friedman et al. | 424/47 |

FOREIGN PATENT DOCUMENTS

WO   PCT/US2006/031356   11/2006

* cited by examiner

*Primary Examiner* — Michael G Hartley
*Assistant Examiner* — Nabila Ebrahim
(74) *Attorney, Agent, or Firm* — Johnathan D Feuchtwang

(57) ABSTRACT

Disclosed is a water-soluble colonoscopy lubricant essentially comprising Polyethylene Glycol 400; Propylene Glycol; and Glycerin. Distilled water may be added as needed to achieve a desired viscosity. Additional ingredients such as a preservative and a pH adjuster may also be added to the colonoscopy lubricant.

1 Claim, 1 Drawing Sheet

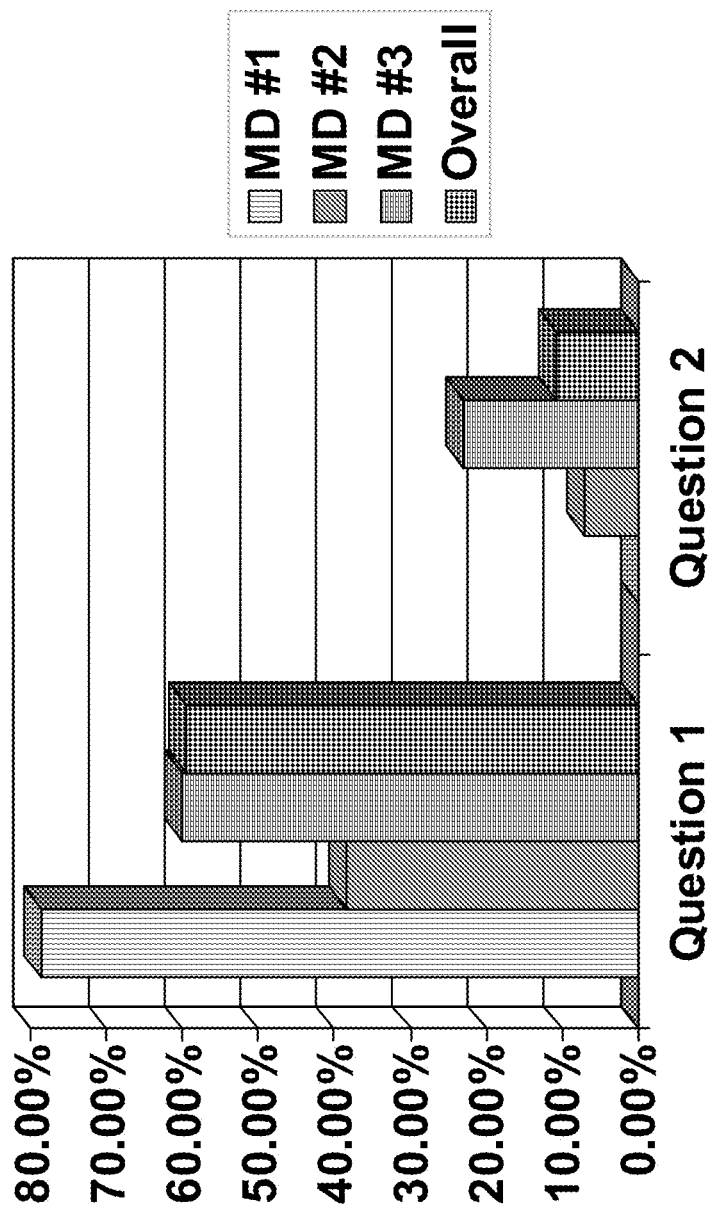

WATER-SOLUBLE COLONOSCOPY LUBRICANT

FIELD OF THE INVENTION

The present invention is directed toward the development of a new agent that enhances the performance of colonoscopy. This enhancement is accomplished by improving the standard lubrication of the tip of the colonoscope that is required during this procedure.

BACKGROUND OF THE INVENTION

The performance of colonoscopy has become a routine method for screening for colon cancer and precancerous lesions (polyps) of the colon. This methodology has been demonstrated to reduce the frequency of advanced colon cancer and to improve overall survival. Currently, colonoscopy is recommended every 10 years for all subjects of average risk (no family history of colon cancer, no symptomatology suggestive of colonic disease such as rectal bleeding, altered bowel habits or weight loss) beginning at age 50.

Individuals having increased risk for colon cancer are recommended to undergo colonoscopy more frequently and at a younger age. Patients diagnosed with precancerous polyps usually undergo the procedure every 3-5 years. The performance of colonoscopy has become routine in many medical centers around the United States and the rest of the developed world.

Although colonoscopy is considered to be safe, a number of potential complications of the procedure exist. These complications include side effects from anesthesia such as hypotension, bradycardia, respiratory depression and mental confusion. Complications of the procedure may also occur due to technical difficulty with the performance of colonoscopy itself. The most severe of these complications is perforation of the colon which occurs in approximately one out of every 2000 procedures performed. Risk factors that predispose to colonic perforation include diverticular disease, prior abdominal or pelvic surgery and severe colitis. Abdominal pain during the procedure and abdominal distention occurring after the procedure are also seen more commonly in patients with diverticular disease, colonic tortuosity, narrowing and angulation. Patients with prior abdominal or pelvic surgery are at higher risk for perforation and may experience more pain and distention with the procedure. These pre-existing factors also make the performance of colonoscopy more difficult and extend the length of time required to complete the examination. When the practitioner performing colonoscopy encounters portions of the colon that are narrowed, angulated, tortuous or show severe diverticulosis causing difficulty in advancement of colonoscope, several maneuvers may be performed to allow safe passage of the colonoscope beyond these difficult areas. External abdominal wall pressure performed by the nurse or support technician may help in advancing the colonoscope beyond the difficult regions of the colon. Changing the position of the patient, for example from a left lateral to a right lateral, prone position or placement on the patient's back may facilitate colonoscope advancement. Recently, the use of colonoscopes with adjustable degrees of stiffness has been shown to improve passage of the colonoscope past these difficult areas.

Practitioners will also utilize a pediatric colonoscope having a smaller diameter and increased flexibility to facilitate the performance of these difficult procedures. Aside from these methods, there presently are no other commonly performed maneuvers to facilitate the performance of colonoscopy, particularly in the patient in which difficulty has been encountered.

Recently, Brocchi, et al. from the department of internal medicine and Gastroenterology at the University of Bologna, Italy performed a study to determine whether performance of colonoscopy could be enhanced by installation of corn oil through the biopsy channel of the colonoscope during the procedure. The biopsy channel provides a direct conduit for instillation of the corn oil and other liquids into the colon.

Patients were divided randomly into two groups. One group underwent standard colonoscopy (with no lubricant instillation), while the other had several small volumes of corn oil instilled through the biopsy channel during performance of the procedure. They found that corn oil installation increased the number of successful intubations of the cecum when compared to the standard performance of colonoscopy. 159 of 168 (95 percent) colonoscopies performed with corn oil installations achieved cecal incubation as compared to only 145 of 170 (85 percent) of successful cecal intubations without corn oil installations. In addition, the level of pain described by the patients was less in the corn oil installation group compared to the control group. The physicians performing colonoscopy also described decreased difficulty of the procedures when corn oil installations were performed. This was the first study demonstrating that the use of a lubricant internally instilled into the colon facilitates the performance of colonoscopy.

Unfortunately, the placement of oils into the biopsy channel of the colonoscope may result in the development of oil residues within the channel following the procedure.

These residues pose a serious risk to patients undergoing colonoscopy as they may provide a nidus for bacterial colonization of the biopsy channels, since residues represent a foreign substance that could enhance bacterial adherence within the biopsy channel of the colonoscope.

Water-soluble ingredients s including glycerin, polyethylene glycol, methylcellulose and others are currently utilized in product formulations needed for the lubrication of gloved fingers and medical instruments inserted into body orifices. These commercial lubricants are highly viscous and formulated in a gel dosage form. These water-soluble lubricants are a mainstay for the simple external lubrication required in common medical practice. However, gel lubricants are too viscous for placement through the biopsy channel of a colonoscope to facilitate the performance of a colonoscopy. In addition, although the aforementioned external lubricating products contain some ingredients that are listed on the Generally Recognized as Safe (GRAS) list of the Food and Drug Administration, these products also contain preservatives and other ingredients that are not approved for human consumption as food additives let alone for placement inside of the colon. Thus, the instillation of currently available lubricants would also be of questionable safety for instillation into the colon. This method is not approved by the FDA.

At present, there is no safe and commercially available water-soluble lubricants developed for use to facilitate the performance of colonoscopy, despite the apparent benefits that such substances would have for patients undergoing colonoscopy and for those involved in the performance of the procedure. Therefore, there is a need to develop methods and compositions that may be used to produce safe, effective agents for installation into the colonoscope for the purpose of lubrication of the colonoscope and enhancement of the procedure.

SUMMARY OF THE INVENTION

A first embodiment of the invention is a water-soluble lubricant essentially comprising: Dimethicone PEG-7 Undecylenate; Polyethylene Glycol 400; and Propylene Glycol. Purified Water may be added to adjust the viscosity of the lubricant. The water-soluble lubricant may be up to about 60% by weight purified water.

According to one aspect of the invention, the aforementioned lubricant may be up to about 20% by weight Dimethicone PEG-7 Undecylenate.

According to another aspect, the water-soluble lubricant may be up to about 15% by weight Polyethylene Glycol 400.

According to another aspect, the water-soluble lubricant of the invention is up to about 4.8% by weight Propylene Glycol.

The water-soluble lubricant may further comprise a pH adjuster such as Triethanolamine. The water-soluble lubricant may further comprise a preservative such as Methylparaben. Alternatively, the preservative may includes one or more ingredients selected from the group (ascorbic acid, ascorbyl palmitate, benzoic acid, calcium sorbate, potassium sorbate, proprionic acid, propylparaben, sodium ascorbate, sodium benzoate, sodium sorbate and tocopherols).

The water-soluble lubricant may further comprise an emulsifying agent. The emulsifying agent may include one or more or salts of cholic acid and desoxycholic acid.

The water-soluble lubricant may further comprise a stabilizer agent. The stabilizer agent may include one or more or of Calcium, potassium compounds and sodium alginate.

Also disclosed is a water-soluble lubricant essentially comprising Polyethylene Glycol 400; Propylene Glycol; and Glycerin. The water-soluble lubricant may further comprise Purified Water. The lubricant may be up to 90% by weight purified water.

According to one aspect of the invention, the aforementioned water-soluble lubricant of claim 18 may be up to 90% by weight Glycerin.

According to one aspect, the water-soluble lubricant is up to about 20% by weight Polyethylene Glycol 400.

According to one aspect the water-soluble lubricant is up to about 4.0% by weight Propylene Glycol.

According to one aspect, the water-soluble lubricant further comprises a pH adjuster such as Triethanolamine.

According to one aspect, the water-soluble lubricant further comprises a preservative such as Methylparaben.

According to one aspect, the water-soluble lubricant further comprises an emulsifying agent. The emulsifying agent may include one or more or salts of cholic acid and desoxycholic acid.

According to one aspect, the water-soluble lubricant further comprises a stabilizer agent. The stabilizer agent may include one or more or of Calcium, potassium compounds and sodium alginate.

BRIEF DESCRIPTION OF THE DRAWINGS

FIG. 1 is a bar chart showing the results of a physician survey.

DETAILED DESCRIPTION OF THE INVENTION

Disclosed is an improved lubricant composition and a method for facilitating the efficacy and tolerance of colonoscopy.

The current invention employs water-soluble lubricants in a liquid form that is easily introduced via a syringe into the biopsy channel of the colonoscope. The substances, instilled by this method, internally lubricate the colon, permitting safer and easier passage of the colonoscope. No oil-based ingredients are used thereby eliminating the risk of residue buildup in the biopsy channels of the colonoscope.

According to one embodiment, the composition is a water soluble lubricant used to facilitate the colonoscope during a colonoscopy. This lubricant could include one or more of the following ingredients: water, an emollient, an emulsifier/humectant, a preservative and a ph adjuster.

A first lubricant composition of the present invention consists essentially of Dimethicone PEG-7 Undecylenate, Polyethylene Glycol 400, and Propylene Glycol. A second lubricant composition of the invention consists essentially of Polyethylene Glycol 400 NF, Propylene Glycol USP and Glycerin, USP.

In any of the lubricant compositions disclosed herein, the viscosity of the lubricant may be adjusted by adding purified water. Additionally, in any of the lubricant compositions disclosed herein, it may be desirable to adjust the pH of the lubricant by adding an optional pH buffer such as phosphate buffer or the like such as is commonly known in the art. Still further, in any of the lubricant compositions disclosed herein, the shelf-life of the product may be enhanced by adding an optional preservative such as Methylparaben or the like such as commonly known in the art. Tables I and II below shows ratios of the aforementioned ingredients found to be effective in facilitating the colonoscopy. It should be understood that Tables I and II detail both the optional ingredients and the essential ingredients necessary to achieve the desired lubricant properties.

One of ordinary skill in the art will readily appreciate that substitutions of one or more ingredients are anticipated and fall within the scope of the invention. However, as noted above, the lubricant formulation of the present invention must be water-soluble to avoid the afore-described problems associated with the use of non-water soluble oils. Therefore, the substitution of the components contributing to the lubricating property of the formulation must also be water-soluble. The substitution of any of the three components functioning as a lubricant in the current formulation cannot simply be replaced with another water-soluble component at the formulated concentration because there are safety consideration that must be taken into account before substituting one component for an another in the formulation. This is mainly due to the sensitivity of the colon and the possible adverse effect that a substituted component may produce after administration. For example, glycerin is a known water-soluble lubricant/wetting agent, but can produce skin irritation when used in a formulation greater than 5%.

The inventor has found that Dimethicone PEG-7 Undecylenate may be replaced by PEG-9 Dimethicone or PEG-9 Grape Seed Phosphate in any of the lubricant compositions disclosed herein. Additionally, in any of the lubricant compositions disclosed herein any of the three primary components (Dimethicone PEG-7 Undecylenate, Polyethylene Glycol 400, and Propylene Glycol) may be substituted with glycerin, sorbitol, or polyethylene glycol with molecular weights ranging from 400 to 3350.

The inventor has found that a 1:1 dilution (water: formulation) provides good results but the other ratios, e.g., 3:1, 2:1 or the like may be appropriate for other applications of the lubricant. Good results have been obtained were the amount of water in the lubricant formulation was increased to 85-90% by weight.

According to the method of the present invention, the substances are regularly instilled during the performance of routine colonoscopy to facilitate performance of the procedure and enhance patient tolerance. The endoscopist may instill additional volumes of the lubricating substances when encountering difficulty in advancement of the colonoscope including angulated portions of the colon, areas with marked diverticular disease, tortuous, redundant or narrowed areas of colon.

According to a presently preferred embodiment, the volume of each instillation is between 45 and 60 mL and 2-4 instillations are required during each colonoscopy.

The lubricant of the invention may include ingredients such as methylcellulose, sorbitol, sodium citrate and sodium hydroxide. The invention will also include any other water-soluble substances that may be incorporated into future forms of the product that enhance the lubricating quality, stability or safety of the product.

Other stabilizing agents and preservatives may also be included in the product. It is anticipated that all ingredients of the product will be contained on the Generally Recognized as Safe (GRAS) list of the Food and Drug Administration or will be considered safe for internal use and/or consumption thus securing the safety of the product.

The current invention employs water-soluble lubricants in a liquid form that may be easily introduced via a syringe into the biopsy channel of the colonoscope.

The substances, instilled by this method, would then internally lubricate the colon, permitting safer and easier passage of the colonoscope. No oil-based ingredients are included, so there will be no risk of residue buildup in the biopsy channels of the colonoscope. Additionally, all ingredients of the product are considered safe for this purpose, thus securing the safety of the product. The substances would regularly be instilled during the performance of routine colonoscopy to facilitate performance of the procedure and enhance patient tolerance. The endoscopist could instill additional volumes of the lubricating substances when encountering difficulty in advancement of the colonoscope.

Additional water-soluble substances that may be incorporated into the product may include ascorbic acid, ascorbyl palmitate, benzoic acid, calcium sorbate, potassium sorbate, proprionic acid, propylparaben, sodium ascorbate, sodium benzoate, sodium sorbate and tocopherols for preservatives.

In addition, salts of cholic acid and desoxycholic acid may be added as emulsifying agents. Calcium, potassium compounds or sodium alginate may be used as stabilizers.

Note that high and low molecular weight PEG may be included as an ingredient.

TABLE I

| Component Description | Quantity per mL | % Formulation by weight/mL | Function |
|---|---|---|---|
| Purified Water | Up to 0.6000 | Up to 60 | Solvent |
| Dimethicone PEG-7 Undecylenate | Up to 0.2000 | Up to 20 | Emollient |
| Polyethylene Glycol 400 | Up to 0.1500 | Up to 15 | Emulsifier/Humectant |
| Propylene Glycol | Up to 0.0480 | Up to 4.8 | Wetting Agent/Humectant |
| Triethanolamine | Up to 0.0020 | Up to 0.2 | Adjust pH |
| Methylparaben | Up to 0.0010 | Up to 0.1 | Preservative |
| Colonglide Solution, Bulk | 1.0010 | 100.1 | — |

TABLE II

| Component Description | Formulation Range (by weight/mL) |
|---|---|
| Purified Water, USP | Up to 90% (0.9000) |
| Polyethylene Glycol 400, NF | Up to 20% (0.2000) |
| Propylene Glycol, USP | Up to 4.0% (0.0400) |
| Glycerin, USP | Up to 3.5% (0.0350) |
| Sodium Phosphate Monobasic, Anhydrous, USP | No range or pH will change |
| Sodium Phosphate Dibasic, Heptahydrate, USP | No range or pH will change |
| Xanthan Gum, NF | Up to 1% (0.0100) |
| Methylparaben, NF | Up to 0.2% (0.0020) |

A study of the enhancement of the performance of colonoscopy by addition of this water soluble lubricant was recently performed.

Study Background

The inventor conducted a pilot study at the Northwest Community Hospital in Arlington Heights Ill. The purpose of the study was to investigate the clinical utility of using a water-soluble lubricant in facilitating the performance of colonoscopy.

Colonoscopy is a routine method to screen for colon cancer and pre-cancerous lesions of the colon. Colonoscopy has been demonstrated to reduce the frequency of advanced colon cancer and to improve survival.

Although colonoscopy is a safe procedure, potential complications of the procedure exist. The most severe of these complications is perforation of the colon. It is estimated that colonic perforation occurs in one out of every 2000 procedures performed. Mortality for perforation is about 7%. Patients also may experience significant abdominal discomfort, pain, and retention of air that is utilized to distend the colon during colonoscopy. Risk factors for these complications include the presence of diverticular disease, colonic tortuosity, narrowing, and angulation. When the practitioner performing colonoscopy encounters portions of the colon that are narrowed, angulated, tortuous, or having severe diverticulosis, difficulty in advancement of the colonoscope often occurs. External abdominal pressure, performed by the nurse or support technician, change of position of the patient, and use of a smaller, more flexible colonoscope, such as a pediatric colonoscope. Some studies have suggested that the use of oil-soluble lubricants may assist in the performance of colonoscopy. These lubricants may result in the development of oil residues within the biopsy channel of the colonoscope. These residues could result in increased risk of transfer of pathogenic bacteria from one patient to another undergoing colonoscopy with the same colonoscope after cleaning. At present, no safe form of lubricant has been developed to facilitate the performance of colonoscopy, despite the apparent benefits that such substances would have for patients undergoing the procedure, and for those involved in the performance of the procedure.

Colonglide™ water-soluble lubricant, a new product that is being developed by Pediatric Pharmaceuticals, in conjunction with its inventor, Dr. Eli Ehrenpreis, is a new combination of water-soluble lubricant ingredients that are similar to surgical lubricants commonly used in medical practice. Colonglide™, lubricant in theory, can be utilized to enhance the performance of colonoscopy. This substance can be injected through the biopsy port of the colonoscope during the performance of colonoscopy. In theory, injection of Colonglide™ lubricant into the lumen of the colon, as a routine during colonoscopy, may facilitate the performance of the procedure. In addition, injection of Colonglide™ lubricant into the lumen of the colon, in areas that are difficult for passage of the colonoscope, represents another method by which these areas can be safely traversed. Finally, the use of Colonglide™ lubricant will potentially reduce the requirement to perform external pressure of the abdomen during colonoscopy. This has additional benefits, since nurses and technicians involved with performing the procedure will not tire themselves or face orthopedic injuries from the repeated external pressure maneuvers that are often required during colonoscopy.

Study Methods

Three gastroenterologists, who are experienced colonoscopists, performed the study. The procedures were performed at the Northwest Community Hospital Gastroenterology Center. All patients who participated in the study were undergoing colonoscopies for screening purposes. One patient was removed from the study when it was found that he had actually had a small intestinal-to-colonic anastomosis.

As originally intended, ten subjects were to be studied by each physician. Additional patients were also enrolled. After the completion of each colonoscopy using the Colonglide, a data sheet was completed by the physician. After the fifth and tenth procedure, a second data sheet was completed. After completion of all cases, a third data sheet was completed. The initial data sheet contained general information about the procedure being performed. The second data sheet contained questions regarding satisfaction with Colonglide. The third data sheet contained information regarding advantages and disadvantages of Colonglide.

While subjects were undergoing standard colonoscopy, 60 mL of Colonglide was instilled in the biopsy channel at the rectosigmoid junction and 60 cc was instilled in the proximal sigmoid colon. In addition, examining physicians were encouraged to give additional doses of Colonglide, as needed, to assist with advancing the colonoscope past difficult areas of the colon, as described above. The use of these additional doses was noted.

Study Results (Also See Charts)

Review of Questionnaire No. 1, Performed After Each Procedure:

Question #1 Facilitation of Colonoscopic Procedure

All three physicians (MD #1, MD#2, MD#3) opinioned that Colonglide facilitated the performance of colonoscopy (Question #1). See FIG. 1. Physician No. 1 stated that Colonglide facilitated the procedure in 11 of 14 cases, or 80%. Physician No. 2 stated that 5 of 13 cases were facilitated by Colonglide, or 38%. Physician No. 3 felt that Colonglide facilitated the procedure in 6 of 10 cases, or 60%. Overall Colonglide facilitated the colonoscopic procedure in 22 of 37 cases performed by the three doctors. This is a 54% facilitation rate.

Question #2 Need for External Pressure

Of note, none of Physician No. 1's patients required external pressure (Question #2); one of Physician No. 2's patients required external pressure, (noted to be a small amount), and three of Physician No. 3's patients required external pressure (two with a small amount, and one with a medium amount of pressure). In total, four of 37 patients, or 11% of patients required external pressure, which appears to be a small number. See FIG. 1.

Additional Doses Used

In six of the colonoscopies performed, more than two 60 mL doses (>120 mL) of Colonglide was utilized. In four of these, 180 mL was utilized. In two of these, 240 mL was utilized. In four out of these six cases, it was noted that Colonglide appeared to facilitate the performance of the procedure.

Time to Reach the Cecum

Although time to reach cecal intubation was noted with these data, without a randomized placebo-controlled trial, it would be difficult to determine whether the average times to cecum were decreased using Colonglide. However, in the vast majority of these cases, the cecum was intubated within five-to-seven minutes. Only four cases took longer than 10 minutes for cecal intubation.

Overall Assessment

This was an initial pilot study to demonstrate the potential utility of Colonglide, a new water-soluble compound that is hypothesized to facilitate the performance of colonoscopy. Advantages of a facilitated procedure include: increased patient safety, decreased use of external pressure maneuvers, and increased efficiency in performing the procedure. The findings of this initial study on the use of Colonglide by three experienced endoscopists confirm the hypothesis that Colonglide is a helpful adjunct to the performance of colonoscopy. The data confirms that Colonglide has the potential of increasing patient safety, reducing the time required to reach the cecum and decreasing the requirement of external pressure maneuvers used during the performance of colonoscopy.

Although this is an open-label trial and may be at risk for bias, these are positive data for the new product Colonglide All three physicians involved in the initial use of Colonglide felt that that this new product facilitated the performance of colonoscopy. Also of great importance, was the apparent decreased requirement for external pressure maneuvers demonstrated in this study.

Summary/Recommendation

These data are highly promising for the further development of Colonglide as a FDA approved product for the gastroenterology market.

The foregoing describes a water-soluble colonoscopy lubricant which includes ingredients listed on the Federal Drug Administration's GRAS list (Generally Recognized As Safe) or which are considered safe for internal use and/or consumption thus securing the safety of the product. Modifications obvious to those skilled in the art can be made without departing from the scope of the present invention.

While the compositions and methods of this invention have been described in terms of preferred embodiments, it will be apparent to those of skill in the art that variations may be applied to the compositions and/or methods and in the steps or in the sequence of the steps of the method described herein, without departing from the concept, spirit, and scope of the invention. More specifically, it will be apparent that certain agents which are both chemically and physiologically related may be substituted for the agents described herein, while the same or similar results would be achieved. All such similar substitutes and modifications apparent to those skilled in the art are deemed to be within the spirit, scope, and concept of the invention, as defined by the appended claims.

The invention claimed is:

1. A water-soluble colonoscopy lubricant consisting of:
Polyethylene Glycol 400;
Purified Water;
Propylene Glycol;
Xanthan gum;

Sodium Phosphate;
Methylparaben;
Propylparaben;
Glycerin;
where the lubricant is up to 90% by weight purified water; and
where the lubricant includes only ingredients generally recognized as safe for human consumption.

* * * * *